(12) United States Patent
Addison et al.

(10) Patent No.: US 12,004,729 B2
(45) Date of Patent: Jun. 11, 2024

(54) METHOD AND SYSTEM FOR USE IN A LUNG ACCESS PROCEDURE TO AID IN PREVENTING PNEUMOTHORAX

(71) Applicant: Bard Peripheral Vascular, Inc., Franklin Lakes, NJ (US)

(72) Inventors: Jordan Addison, Chandler, AZ (US); Nicholas Mowrey, Phoenix, AZ (US); Heather Storm, Phoenix, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 266 days.

(21) Appl. No.: 17/537,927

(22) Filed: Nov. 30, 2021

(65) Prior Publication Data
US 2022/0087667 A1    Mar. 24, 2022

Related U.S. Application Data

(62) Division of application No. 16/657,260, filed on Oct. 18, 2019, now Pat. No. 11,219,435.

(51) Int. Cl.
*A61B 17/34* (2006.01)
*A61B 17/00* (2006.01)
*A61L 24/04* (2006.01)

(52) U.S. Cl.
CPC .... *A61B 17/00491* (2013.01); *A61B 17/3421* (2013.01); *A61L 24/046* (2013.01); *A61B 2017/00367* (2013.01); *A61B 2017/00495* (2013.01); *A61B 2017/00557* (2013.01); *A61B 2017/00809* (2013.01); *A61B 2017/3419* (2013.01)

(58) Field of Classification Search
CPC ... A61B 17/00; A61B 17/34; A61B 17/00491; A61B 17/3421; A61B 17/0057; A61B 2017/00495; A61B 2017/00809; A61B 2017/00557; A61B 2017/3419; A61B 2017/00637
See application file for complete search history.

(56) References Cited

U.S. PATENT DOCUMENTS

| | | | |
|---|---|---|---|
| 5,445,167 A * | 8/1995 | Yoon | A61B 17/0057 606/139 |
| 6,325,067 B1 * | 12/2001 | Sterman | A61B 17/0218 128/898 |
| 6,461,294 B1 | 10/2002 | Oneda et al. | |

(Continued)

*Primary Examiner* — Vi X Nguyen
(74) *Attorney, Agent, or Firm* — Dinsmore & Shohl LLP

(57) ABSTRACT

A method for use in a lung access procedure to aid in preventing pneumothorax includes providing a cannula having a pair of balloons, the pair of balloons including a first balloon longitudinally spaced from a second balloon along the cannula; inserting the cannula along an access opening and through pleural layers of a patient, with the first balloon and the second balloon of the pair of balloons respectively positioned on opposite sides of the pleural layers; inflating the pair of balloons with a first amount of a two-component sealant to compress the pleural layers together; and inflating the pair of balloons with a second amount of the two-component sealant that is sufficient to rupture the pair of balloons so as to comingle a first sealant component and a second sealant component of the two-component sealant at the site of the pleural layers so as to adhere the pleural layers together.

10 Claims, 5 Drawing Sheets

(56) References Cited

U.S. PATENT DOCUMENTS

| | | |
|---|---|---|
| 6,602,204 B2 | 8/2003 | Dubrul et al. |
| 6,770,070 B1 | 8/2004 | Balbierz |
| 8,163,034 B2 | 4/2012 | Chang et al. |
| 8,608,724 B2 | 12/2013 | Roschak |
| 8,709,034 B2 | 4/2014 | Keast et al. |
| 8,734,362 B2 | 5/2014 | Boyle, Jr. |
| 8,764,725 B2 | 7/2014 | Averbuch |
| 8,845,518 B2 | 9/2014 | Oneda et al. |
| 8,932,326 B2 | 1/2015 | Riina et al. |
| 9,295,818 B2 | 3/2016 | Riina et al. |
| 9,533,128 B2 | 1/2017 | Kramer et al. |
| 9,986,893 B2 | 6/2018 | Cornhill et al. |
| 10,111,683 B2 | 10/2018 | Tsamir et al. |
| 10,272,260 B2 | 4/2019 | Kaplan et al. |
| 11,219,435 B2 * | 1/2022 | Addison ............... A61L 24/043 |
| 2012/0053485 A1 | 3/2012 | Bloom |
| 2013/0226026 A1 | 8/2013 | Dillard et al. |
| 2014/0142620 A1 | 5/2014 | Marchi et al. |
| 2016/0279388 A1 | 9/2016 | Barrish et al. |

\* cited by examiner

METHOD AND SYSTEM FOR USE IN A LUNG ACCESS PROCEDURE TO AID IN PREVENTING PNEUMOTHORAX

CROSS-REFERENCE TO RELATED APPLICATIONS

This is a divisional of application Ser. No. 16/657,260 filed Oct. 18, 2019, which is incorporated by reference in its entirety.

TECHNICAL FIELD

The present invention relates to a lung access procedure, such as a lung biopsy, and, more particularly, to a method and system for use in a lung access procedure to aid in preventing pneumothorax.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is a method and system for use in a lung access procedure to aid in preventing pneumothorax.

SUMMARY OF INVENTION

The present invention provides a method and system for use in a lung access procedure to aid in preventing pneumothorax.

The invention, in one form, is directed to a method for use in a lung access procedure to aid in preventing pneumothorax, including providing a cannula having a pair of balloons, the pair of balloons including a first balloon longitudinally spaced from a second balloon along the cannula; inserting the cannula along an access opening and through pleural layers of a patient, with the first balloon and the second balloon of the pair of balloons respectively positioned on opposite sides of the pleural layers; inflating the pair of balloons with a first amount of a two-component sealant to compress the pleural layers together; and inflating the pair of balloons with a second amount of the two-component sealant that is sufficient to rupture the pair of balloons so as to comingle a first sealant component and a second sealant component of the two-component sealant at the site of the pleural layers so as to adhere the pleural layers together.

The invention, in another form, is directed to a system for use in a lung access procedure to aid in preventing pneumothorax. The system includes a cannula that has a cannula hub, an elongate cannula shaft, a first balloon, a second balloon, and a lumen that extends through each of the cannula hub and the elongate cannula shaft. The elongate cannula shaft has a proximal end portion and a distal end portion. The proximal end portion is connected to the cannula hub. The first balloon is longitudinally spaced from the second balloon along the distal end portion of the cannula. Each of the first balloon and the second balloon is connected to the elongate cannula shaft. The elongate shaft has a first elongate passage in fluid communication with the first balloon and a second elongate passage in fluid communication with the second balloon. The cannula hub is configured to define a first sealant port and a second sealant port. The first sealant port is in fluid communication with the first elongate passage and the first balloon. The second sealant port is in fluid communication with the second elongate passage and the second balloon. A sealant applicator is configured to separately carry each of a first sealant component of a two-component sealant and a second sealant component of the two-component sealant. The sealant applicator has a first applicator port that is configured to deliver the first sealant component. The first applicator port is configured to be connected in fluid communication with the first sealant port of the cannula hub of the cannula. The sealant applicator has a second applicator port that is configured to deliver the second sealant component. The second applicator port is configured to be connected in fluid communication with the second sealant port of the cannula hub of the cannula. The sealant applicator has an actuator. A first actuation of the actuator delivers a first amount of the first sealant component to the first balloon to inflate the first balloon, and delivers a first amount of the second sealant component to the second balloon to inflate the second balloon. A second actuation of the actuator delivers a second amount of the first sealant component to the first balloon to rupture the first balloon, and delivers a second amount of the second sealant component to the second balloon to rupture the second balloon.

An advantage of the present invention is that the same pair of balloons used to compress the pleural layers also is used to deliver and comingle the two-component sealant at the pleural layer site, external to the pair of balloons.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
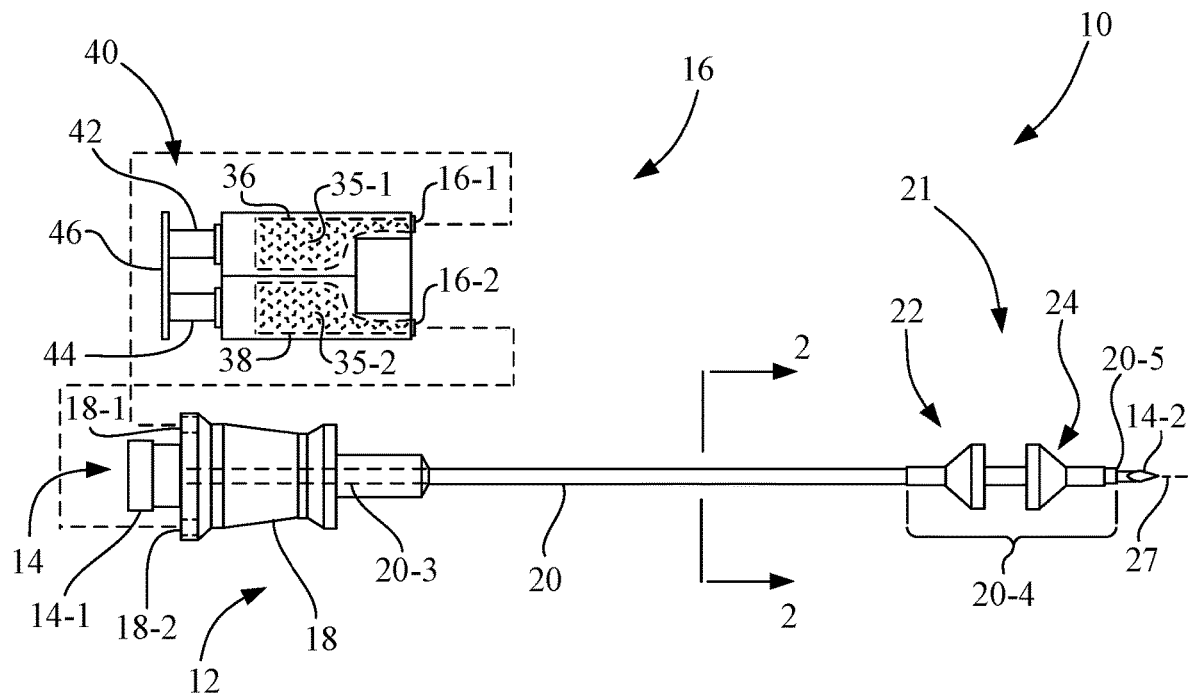
FIG. 1 is a side view of a system for use in a lung access procedure to aid in preventing pneumothorax, wherein the system includes a cannula that carries a balloon assembly having a pair of balloons, and a sealant applicator for supplying a two-component sealant to the pair of balloons, in accordance with an aspect of the present invention.

Referring now to drawings, and more particularly to FIG. 1, there is shown a system 10 for use in a lung access procedure to aid in preventing pneumothorax.

In present embodiment, system 10 includes a cannula 12, a stylet 14, and a sealant applicator 16.

Cannula 12 includes a cannula hub 18, an elongate cannula shaft 20, and a balloon assembly 21 having pair of balloons 22, 24 that includes a first balloon 22 and a second balloon 24. Cannula 12 also has a lumen 26 that extends through each of cannula hub 18 and elongate cannula shaft 20.

Stylet 14 is slidably received in lumen 26 of cannula 12, such that cannula 12 and stylet 14 are coaxial along a longitudinal axis 27. Stylet 14 includes a stylet hub 14-1 and a penetrating end portion 14-2. Stylet 14 is sized such that penetrating end portion 14-2 extends beyond a longitudinal extent of cannula 12.

Figure 2:
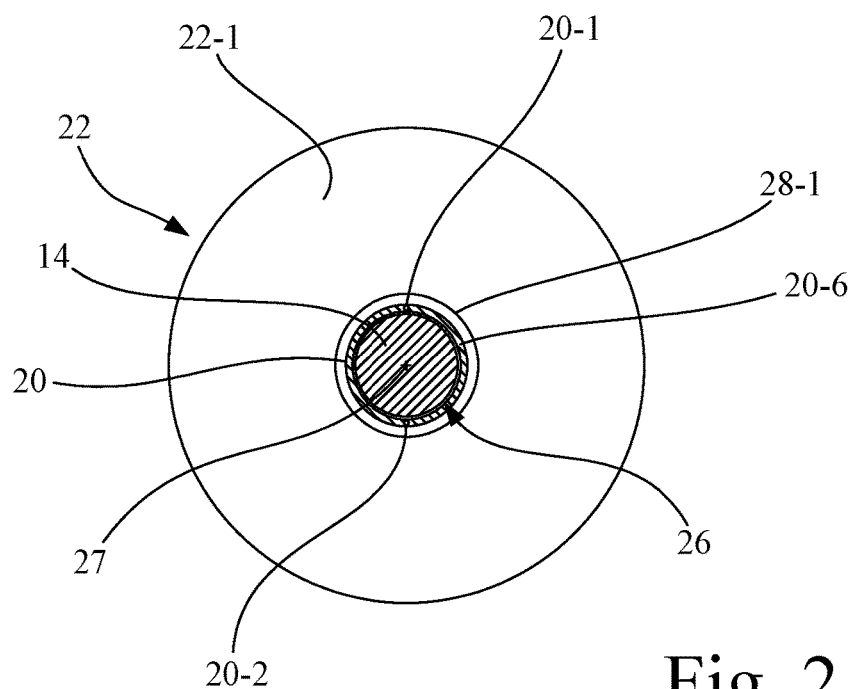
FIG. 2 is a section view of the cannula and stylet of FIG. 1, taken along line 2-2 of FIG. 1, that shows the first and second elongate passages in the side wall of the cannula.

Referring to FIGS. 1 and 2, elongate cannula shaft 20 of cannula 12 has a first elongate passage 20-1, a second elongate passage 20-2, a proximal end portion 20-3, a distal end portion 20-4, a distal end 20-5, and a side wall 20-6. In the present embodiment, first elongate passage 20-1 and second elongate passage 20-2 may be located in the side wall 20-6 of elongate cannula shaft 20. However, alternatively, first elongate passage 20-1 and second elongate passage 20-2 may be formed as separate tubes attached to side wall 20-6 of elongate cannula shaft 20.

Proximal end portion 20-3 of elongate cannula shaft 20 is connected to cannula hub 18. First balloon 22 is longitudinally spaced from second balloon 24 along distal end portion 20-4 of elongate cannula shaft 20 of cannula 12, wherein each of first balloon 22 and second balloon 24 is connected to elongate cannula shaft 20. First elongate passage 20-1 is in fluid communication with first balloon 22, e.g., via an orifice (not shown) in side wall 20-6 of elongate cannula shaft 20, that connects first elongate passage 20-1 with an interior of first balloon 22. Likewise, second elongate passage 20-2 is in fluid communication with second balloon 24, e.g., via another orifice (not shown) in side wall 20-6 of elongate cannula shaft 20, that connects second elongate passage 20-2 with an interior of second balloon 24.

Cannula hub 18 may be, for example, a Luer-type fitting, and is configured to define a first sealant port 18-1 and a second sealant port 18-2. First sealant port 18-1 is in fluid communication with first elongate passage 20-1 and first balloon 22. Second sealant port 18-2 is in fluid communication with second elongate passage 20-2 and second balloon 24.

Figure 3:
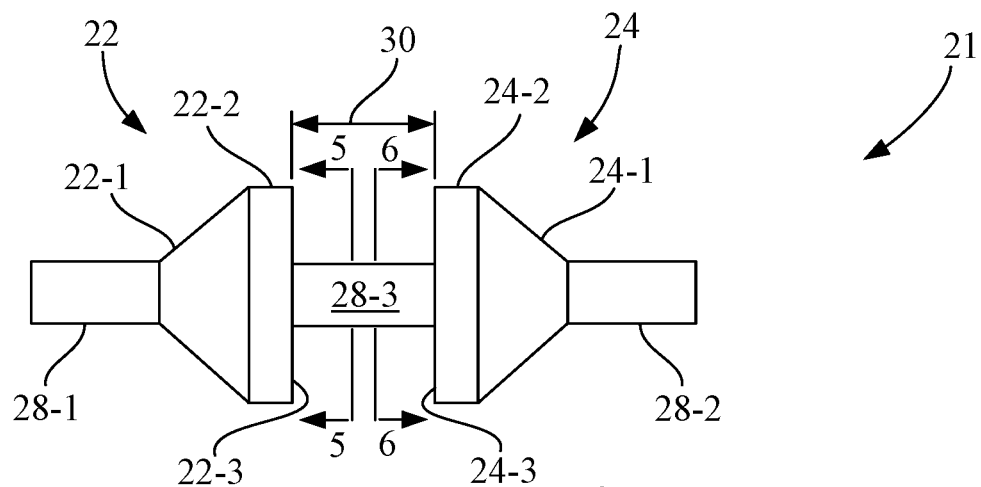
FIG. 3 is an enlarged side view of the balloon assembly of FIG. 1, showing the pair of balloons in an inflated state.
Figure 4:
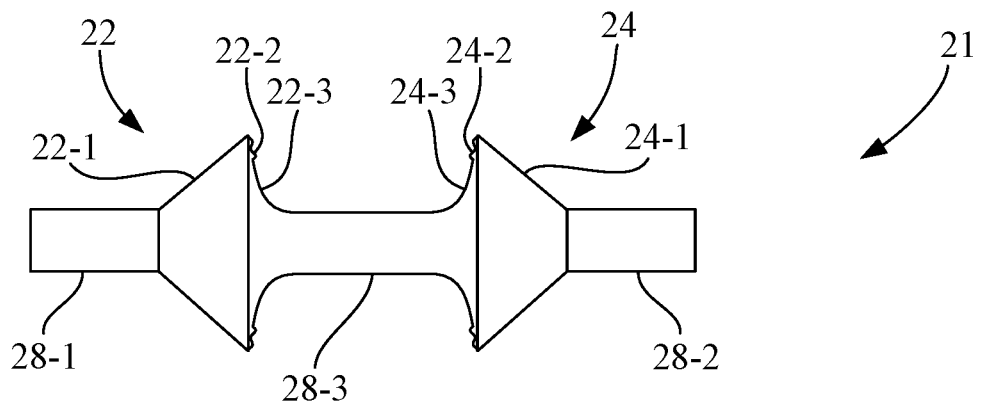
FIG. 4 is an enlarged side view of the balloon assembly of FIG. 1, showing the pair of balloons in an non-inflated state.

FIG. 3 shows balloon assembly 21 having the pair of balloons 22, 24 in an inflated state, and FIG. 4 shows balloon assembly 21 having the pair of balloons 22, 24 in a non-inflated state. Balloon assembly 21 may be formed as an integral structure, and may include mounting portions 28-1 and 28-2, and a connector member 28-3. Mounting portions 28-1 and 28-2 are tubular members that longitudinally extend from each of first balloon 22 and second balloon 24, respectively. Connector member 28-3 is configured to connect, and longitudinally space, first balloon 22 and second balloon 24. In the present embodiment, each of mounting portions 28-1 and 28-2, and connector member 28-3, may be in the form of a tube that is received over, and attached to, distal end portion 20-4 of elongate cannula shaft 20 of cannula 12.

Balloon assembly 21 having the pair of balloons 22, 24, the mounting portions 28-1 and 28-2, and connector member 28-3, may be made from a polymeric material, such as for example, a polyester material, such as Mylar® that is available from E.I. DuPont Corporation.

First balloon 22 includes a first side wall 22-1, a first bellows portion 22-2, and a first engagement surface 22-3. First bellows portion 22-2 is interposed between, and connected to each of, first side wall 22-1 and first engagement surface 22-3. In the present embodiment, first side wall 22-1 may be a rigid structure; however, it is contemplated that first side wall 22-1 may be formed to be rigid, semi-rigid, or collapsible by varying a degree of stiffness of first side wall 22-1, e.g., by increasing or decreasing a thickness of first side wall 22-1 and/or by material selection. First bellows portion 22-2 may be constructed, for example, as a flexible membrane that interconnects first side wall 22-1 and first engagement surface 22-3. Fluid communication between first elongate passage 20-1 of elongate cannula shaft 20 and an interior of first balloon 22 may be, for example, through a respective orifice in side wall 20-6 of elongate cannula shaft 20 of cannula 12 and/or a respective aperture in mounting portion 28-1.

In the present embodiment, first side wall 22-1 is configured as a frustoconical member having a frustoconical shape, and is annularly disposed around mounting portion 28-1. Also, in the present embodiment, first engagement surface 22-3 is substantially planar when inflated, and is annularly disposed around connector member 28-3. The term "substantially planar" may be in a range, for example, of planar to slightly domed, wherein slightly domed may be a curvature having a longitudinal radius at least two times the length of first balloon 22.

As shown in FIG. 4, when first balloon 22 is not inflated, first bellows portion 22-2 and first engagement surface 22-3 are collapsed. As shown in FIG. 3, when first balloon 22 is inflated, first engagement surface 22-3 is projected axially from first side wall 22-1 to form a substantially planar surface, and first bellows portion 22-2 is expanded.

Second balloon 24 includes a second side wall 24-1, a second bellows portion 24-2, and a second engagement surface 24-3. Second bellows portion 24-2 is interposed between, and connected to each of, second side wall 24-1 and second engagement surface 24-3. In the present embodiment, second side wall 24-1 may be a rigid structure; however, it is contemplated that second side wall 24-1 may be formed to be rigid, semi-rigid, or collapsible by varying a degree of stiffness of second side wall 24-1, e.g., by increasing or decreasing a thickness of second side wall 24-1 and/or by material selection. Second bellows portion 24-2 may be constructed, for example, as a flexible membrane that interconnects second side wall 24-1 and second engagement surface 24-3. Fluid communication between second elongate passage 20-2 of elongate cannula shaft 20 and an interior of second balloon 24 may be, for example, through a respective orifice in side wall 20-6 of elongate cannula shaft 20 of cannula 12 and/or a respective aperture in mounting portion 28-2.

In the present embodiment, second side wall 24-1 is configured as a frustoconical member having a frustoconical shape, and is annularly disposed around mounting portion 28-2. Also, in the present embodiment, second engagement surface 24-3 is substantially planar when inflated, and is annularly disposed around connector member 28-3. The term "substantially planar" may be in a range, for example, of planar to slightly domed, wherein slightly domed may be a curvature having a longitudinal radius at least two times the length of second balloon 24.

As shown in FIG. 4, when second balloon 24 is not inflated, second bellows portion 24-2 and second engagement surface 24-3 are collapsed. As shown in FIG. 3, when second balloon 24 is inflated, second engagement surface 24-3 is projected axially from second side wall 24-1 to form a substantially planar surface, and second bellows portion 24-2 is expanded.

Accordingly, when the pair of balloons 22, 24 are inflated, each of first engagement surface 22-3 of first balloon 22 and second engagement surface 24-3 of second balloon 24 are substantially planar, and face each other across a gap 30. Gap 30 is a distance selected to correspond generally to the thickness of the pleural layers 58, 62 (see FIG. 7), e.g., in a range of 5 millimeters (mm) to 10 mm.

Figures 5, 6:
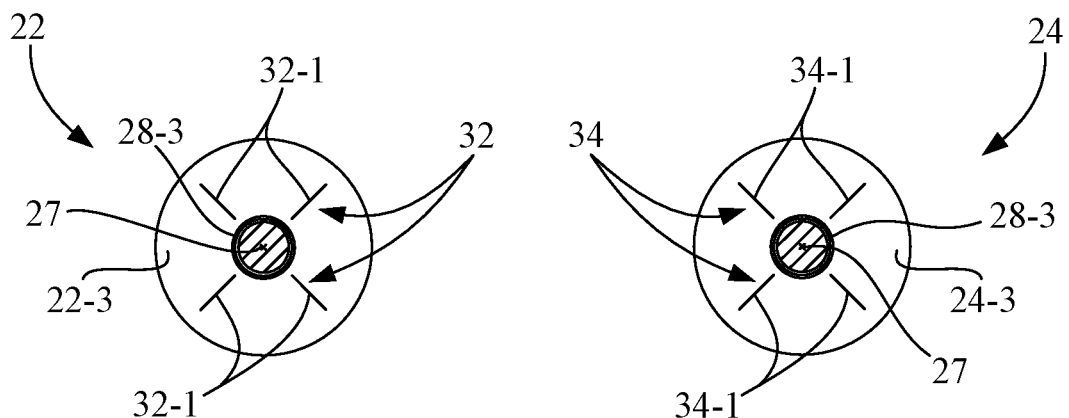
FIG. 5 is a section view of the balloon assembly taken along line 5-5 of FIG. 3, that shows the rupture location of the engagement surface of the first balloon of the pair of balloons.
FIG. 6 is a section view of the balloon assembly taken along line 6-6 of FIG. 3, that shows the rupture location of the engagement surface of the second balloon of the pair of balloons.

Referring also to FIG. 5, in the present embodiment, first engagement surface 22-3 of first balloon 22 is configured to define a rupture location 32 of first balloon 22. Referring also to FIG. 6, in the present embodiment, second engagement surface 24-3 of second balloon 24 is configured to define a rupture location 34 of second balloon 24. Rupture location 32 of first balloon 22 may be, for example, at least one channel 32-1 formed in a surface of first balloon 22 so as to control a location of the rupture of first balloon 22 due to an intentional over inflation. Likewise, rupture location 34 of second balloon 24 may be, for example, at least one channel 34-1 formed in a surface of first balloon 22 so as to control a location of the rupture of second balloon 24 due to an intentional over inflation. Each of channel 32-1 and channel 34-1 is a thinning of the material of the respective balloon 22, 24, and may include multiple non-interconnecting troughs, as shown.

In the present embodiment, each of channel 32-1 and channel 34-1 is arranged as an X-shape, although it is contemplated that other shapes may also be used to define rupture location 32 of first balloon 22 and rupture location 34 of second balloon 24. Also, it is contemplated that rupture location 32 of first balloon 22 and rupture location 34 of second balloon 24 may be located in other portions of first balloon 22 and second balloon 24. For example, it is contemplated that, alternatively, rupture location 32 may be formed in at least one of first side wall 22-1, first bellows portion 22-2, and first engagement surface 22-3 of first balloon 22; and likewise, it is contemplated that, alternatively, rupture location 34 may be formed in at least one of second side wall 24-1, second bellows portion 24-2, and second engagement surface 24-3 of second balloon 24.

Referring again to FIG. 1, sealant applicator 16 is configured to separately carry each of a first sealant component 35-1 of a two-component sealant and a second sealant component 35-2 of the two-component sealant. When the first sealant component 35-1 comingles with the second sealant component 35-2, the resulting chemical reaction forms a sealant gel suitable to seal the pleural layers 58, 62 (see FIG. 7) together. The first sealant component 35-1 may include, for example, at least two N-hydroxysuccinimide (NHS) ester groups, and second sealant component 35-2 may include, for example, at least two amine groups. For example, the first sealant component 35-1 may be a solution containing polyethylene glycol (PEG) succinimidyl succinate and the second sealant component 35-2 may be a solution containing at least one of albumin, polyethylenimine (PEI), and a functionalized PEG that has at least two amine groups.

In the present embodiment, for example, sealant applicator 16 is in the form of a syringe-type applicator having a first sealant chamber 36 and a second sealant chamber 38. First sealant chamber 36 contains the first sealant component 35-1 of the two-component sealant, and a second sealant chamber 38 contains the second sealant component 35-2 of the two-component sealant.

First sealant chamber 36 has a first applicator port 16-1. First applicator port 16-1 is configured to be connected in fluid communication with first sealant port 18-1 of cannula hub 18 of cannula 12, and is configured to deliver the first sealant component 35-1 to first balloon 22 of cannula 12 via first elongate passage 20-1 of cannula 12 (see also FIG. 2).

Second sealant chamber 38 has a second applicator port 16-2. Second applicator port 16-2 is configured to be connected in fluid communication with second sealant port 18-2 of cannula hub 18 of cannula 12, and is configured to deliver the second sealant component 35-2 to second balloon 24 of cannula 12 via second elongate passage 20-2 of cannula 12.

Sealant applicator 16 further includes an actuator 40, wherein a first actuation of actuator 40 delivers a first amount of the first sealant component 35-1 to first balloon 22 to inflate first balloon 22, and delivers a first amount of the second sealant component 35-2 to second balloon 24 to inflate second balloon 24. A second actuation of actuator 40 delivers a second amount of first sealant component 35-1 to first balloon 22 to rupture first balloon 22, and delivers a second amount of second sealant component 35-2 to second balloon 24 to rupture second balloon 24.

The first amount is a predetermined amount, e.g., volume, of each of the first sealant component 35-1 and the second sealing component 35-2 needed to fully inflate each of first balloon 22 and second balloon 24, respectively, and the second amount is an amount, e.g., volume, e.g., also predetermined, of each of the first sealant component 35-1 and the second sealing component 35-2 needed to rupture first balloon 22 and to rupture second balloon 24, respectively. For example, to establish full inflation of first balloon 22 and second balloon 24, the first amount may be, for example, 0.5 milliliters (ml) of each of the first sealant component 35-1 and of the second sealant component 35-2. To establish a rupture of each of first balloon 22 and second balloon 24, the second amount may be an additional 0.1 ml of each of the first sealant component 35-1 and the second sealant component 35-2, i.e., for a total of 0.6 ml of each of the first sealant component 35-1 and the second sealant component 35-2.

While in the present embodiment, the first amount of the first sealant component 35-1 and the first amount of the second sealant component 35-2 are the same, it is contemplated that ratios other than 1:1 may be used. Likewise, while in the present embodiment, the second amount of the first sealant component 35-1 and the second amount of the second sealant component 35-2 are the same, it is contemplated that ratios other than 1:1 may be used.

In the present embodiment, actuator 40 of sealant applicator 16 includes a first piston 42, a second piston 44, and a plunger handle 46 connected to each of first piston 42 and second piston 44. First piston 42 is slidable within first sealant chamber 36, and is located proximal to the first sealant component 35-1 of the two-component sealant. Second piston 44 is slidable within second sealant chamber 38, and is located proximal to the second sealant component 35-2 of the two-component sealant.

When plunger handle 46 is depressed a first distance, the first amount of the first sealant component 35-1 is delivered from first sealant chamber 36 to first balloon 22 to inflate first balloon 22, and the first amount of the second sealant component 35-2 is delivered from second sealant chamber 38 to second balloon 24 to inflate second balloon 24. The first amount may be, for example, 0.5 milliliters (ml) of each of the first sealant component 35-1 and the second sealant component 35-2.

When plunger handle 46 is depressed a second distance beyond the first distance, the second amount of the first sealant component 35-1 is delivered from first sealant chamber 36 to first balloon 22 to rupture first balloon 22, and the second amount of the second sealant component 35-2 is delivered from second sealant chamber 38 to second balloon 24 to rupture second balloon 24. The second amount is variable, and depends upon a total amount of the two-component sealant that the physician wants to be delivered. For example, if the first amount is 0.5 ml of each of the first sealant component 35-1 and the second sealant component 35-2 to establish full inflation of the pair of balloons 22, 24, then the second amount may be an additional 0.1 ml of each of the first sealant component 35-1 and the second sealant component 35-2 to rupture the pair of balloons 22, 24, i.e., for a total of 0.6 ml of each of the first sealant component 35-1 and the second sealant component 35-2.

Figure 7:
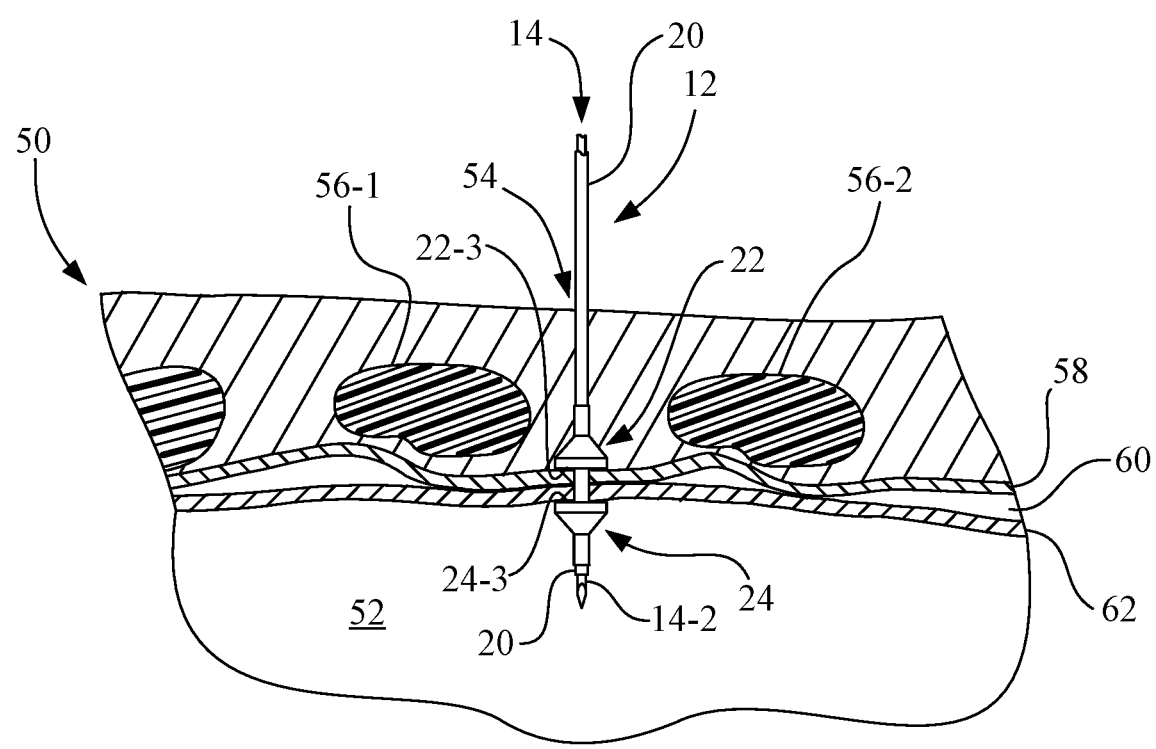
FIG. 7 depicts a section view of a portion of a chest wall and lung of a patient, and shows a side view of the cannula and the pair of balloons in the inflated state to compress the pleural layers together.

Referring to FIG. 7, there is depicted a portion of a chest wall 50 and lung 52 of a patient. Cannula 12 and stylet 14 are used, in combination, to form an access opening 54 to the interior of lung 52. In particular, access opening 54 is formed between adjacent ribs 56-1, 56-2 in the rib cage of chest wall 50, and extends though the parietal pleura 58, the pleural space 60, and the visceral pleura 62 to provide access to the interior of the lung 52. Collectively, parietal pleura 58 and visceral pleura 62 are referred to herein as the pleural layers 58, 62. Cannula 12 is shown positioned in access opening 54, with first balloon 22 located proximal to (and adjacent), i.e., above, parietal pleura 58, and with second balloon 24 located distal to (and adjacent), i.e., below, the visceral pleura 62. The location of first balloon 22 and second balloon 24 relative to the pleural layers 58, 62 may be determined and/or confirmed, using an imaging system, such as for example, ultrasound imaging or X-ray imaging. FIG. 7 shows the pair of balloons 22, 24 in an inflated state, so as to compress the pleural layers 58, 62.

Figure 8:
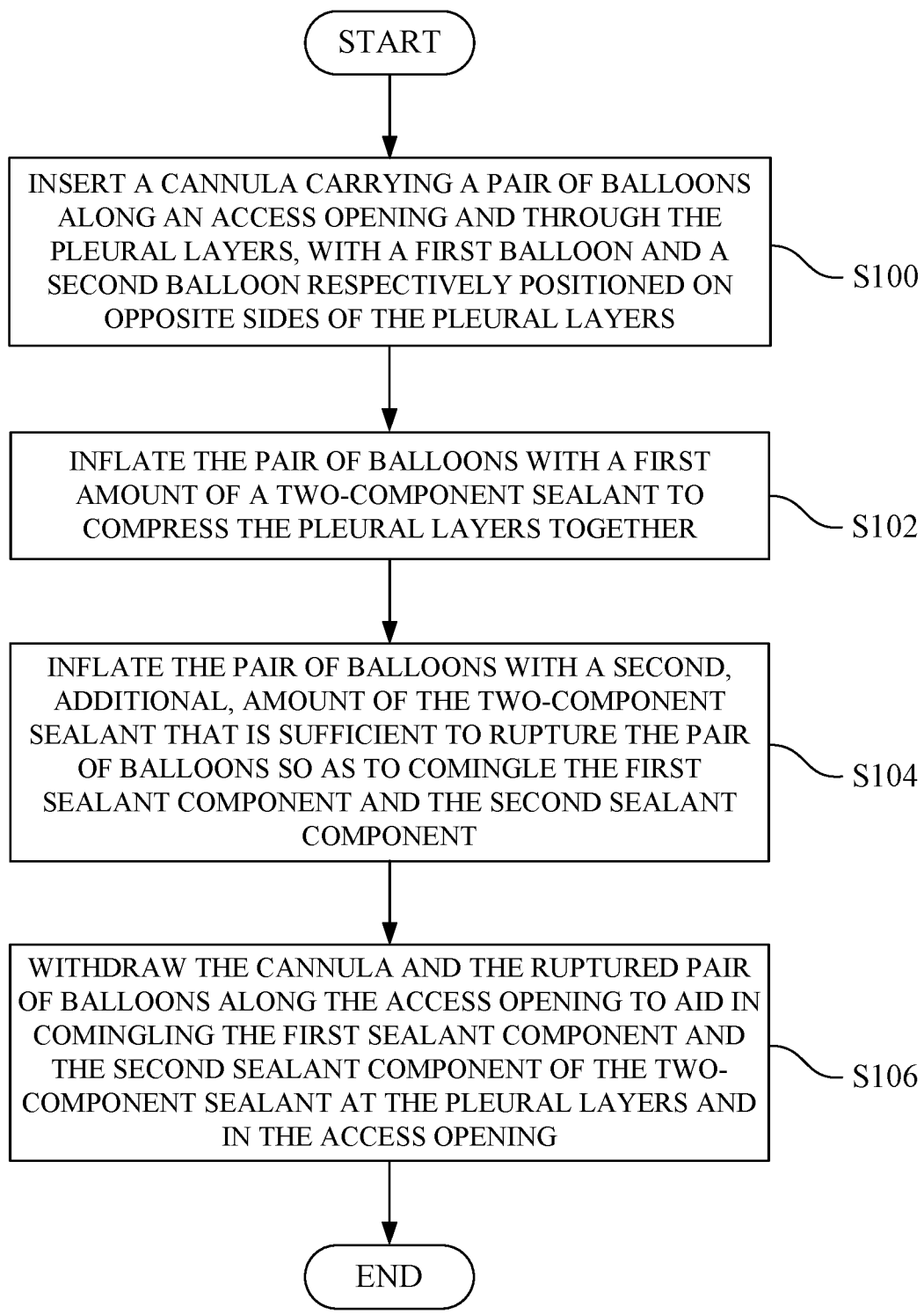
FIG. 8 is a flowchart of a method of using the system of FIG. 1 for use in a lung access procedure to aid in preventing pneumothorax.

FIG. 8 is a flowchart of a method for use in a lung access procedure to aid in preventing pneumothorax. The method will be described, and best understood, with further reference to FIGS. 1 and 7.

At step S100, cannula 12 carrying the pair of balloons 22, 24 is inserted, alone or in combination with stylet 14, along access opening 54 and through the pleural layers 58, 62 of a patient, with first balloon 22 and second balloon 24 of the pair of balloons 22, 24 respectively positioned on opposite sides of the pleural layers 58, 62.

At step S102, using sealant applicator 16, the pair of balloons 22, 24 are inflated with the first amount of the two-component sealant to compress the pleural layers 58, 62 together, as depicted in FIG. 7. Step S102 may be performed, for example, by connecting sealant applicator 16 to cannula 12, and actuating the actuator 40 of sealant applicator 16 to simultaneously supply the first sealant component 35-1 of the two-component sealant to first balloon 22 and supply the second sealant component 35-2 of two-component sealant to the second balloon 24.

At this time, with pleural layers 58, 62 compressed, lung tissue may be accessed via lumen 26 of cannula 12 to perform a lung procedure, e.g., a lung biopsy, may be performed through lumen 26 of cannula 12 by removing sealant applicator 16 from cannula hub 18 and removing stylet 14 from lumen 26 of cannula 12.

At step S104, after reinstalling sealant applicator 16, for example (if previously removed), a second actuation of sealant applicator 16 inflates the pair of balloons 22, 24 with a second, i.e., additional, amount of the two-component sealant that is sufficient to rupture the pair of balloons 22, 24 so as to comingle the first sealant component 35-1 and the second sealant component 35-2 of the two-component sealant to form a sealant gel at the site of the pleural layers 58, 62, so as to adhere the pleural layers 58, 62 together.

Step S104 may be performed, for example, by connecting sealant applicator 16 to cannula 12, and performing a second actuation the actuator 40 of sealant applicator 16 to simultaneously supply the second amount of the first sealant component 35-1 of the two-component sealant to first balloon 22 to rupture first balloon 22, and to supply the second amount of second sealant component 35-2 of two-component sealant to second balloon 24 to rupture second balloon 24.

At step S106, cannula 12 and the ruptured pair of balloons 22, 24 are withdrawn along access opening 54 to aid in comingling the first sealant component 35-1 and the second sealant component 35-2 of the two-component sealant at the pleural layers 58, 62 and in access opening 54. In one implementation of the method, step S106, i.e., the step of withdrawing, will immediately follow the step S104 that results in the rupture of the pair of balloons 22, 24.

Figure 9:
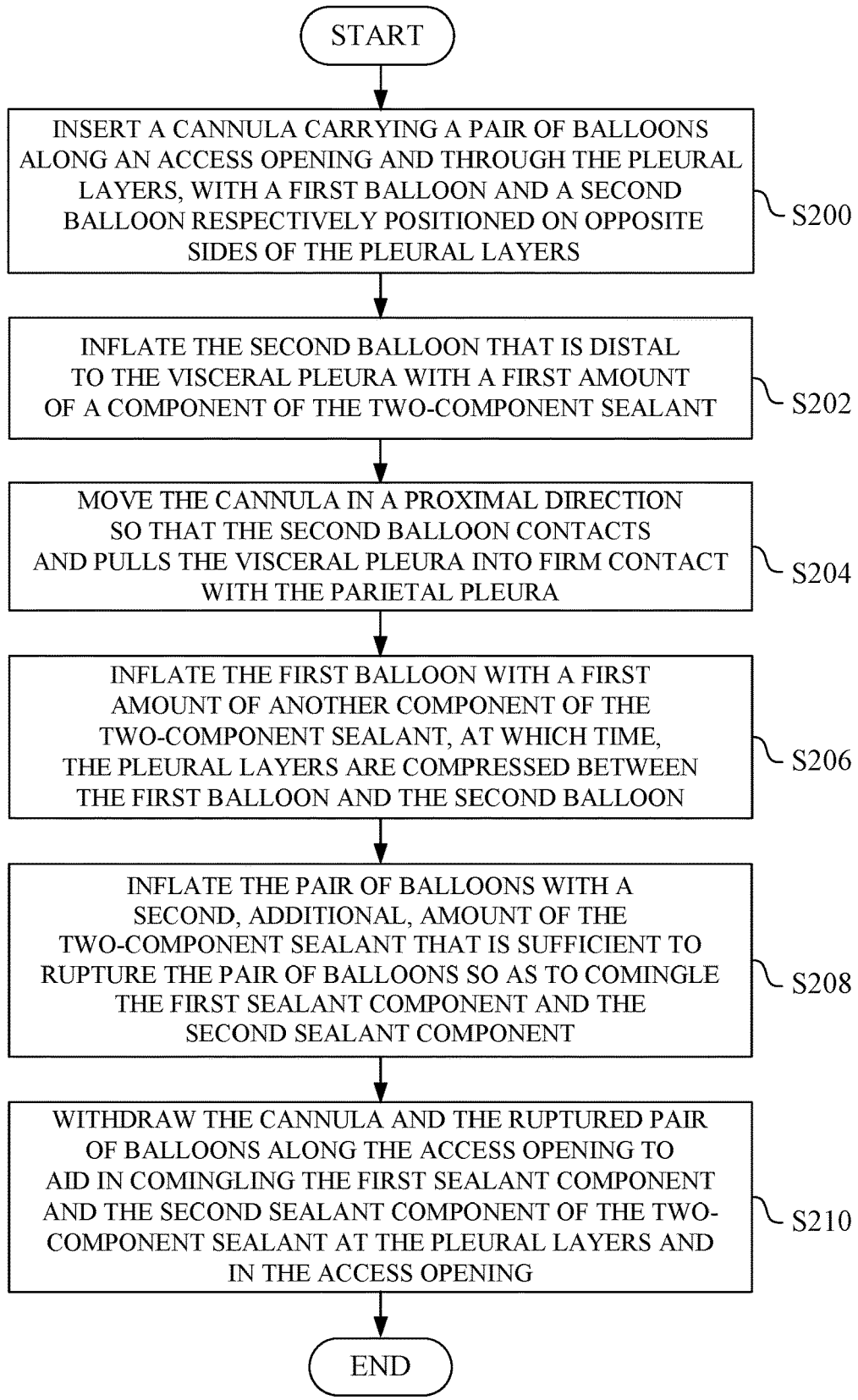
FIG. 9 is a flowchart of another method of using the system of FIG. 1, modified such that the pistons of the sealant applicator are separately actuatable, for use in a lung access procedure to aid in preventing pneumothorax.

FIG. 9 is a flowchart of another method for use in a lung access procedure to aid in preventing pneumothorax. The method will be described, and best understood, with further reference to FIGS. 1 and 7. In practicing the method of FIG. 9, system 10 of FIG. 1 is modified to remove plunger handle 46, so that first piston 42 and second piston 44 are separately actuatable.

At step S200, cannula 12 carrying the pair of balloons 22, 24 is inserted, alone or in combination with stylet 14, along access opening 54 and through the pleural layers 58, 62 of a patient, with first balloon 22 and second balloon 24 of the pair of balloons 22, 24 respectively positioned on opposite sides of the pleural layers 58, 62. In this configuration, second balloon 24 is distal to visceral pleura 62.

At step S202, using sealant applicator 16, second balloon 24 is inflated with a first amount of a component of a two-component sealant. Step S202 may be performed, for example, by connecting sealant applicator 16 to cannula 12, and actuating second piston 44 of sealant applicator 16 to supply the second sealant component 35-2 of the two-component sealant to the second balloon 24.

At step S204, cannula 12 is moved by the user, i.e., pulled, in a proximal direction so that second balloon 24 contacts and pulls visceral pleura 62 into firm contact with parietal pleura 58.

At step S206, using sealant applicator 16, first balloon 22 is inflated with a first amount of another component of the two-component sealant. Step S206 may be performed, for example, by actuating first piston 42 of sealant applicator 16 to supply the first sealant component 35-1 of the two-component sealant to first balloon 22.

At this time, with pleural layers 58, 62 being compressed between first balloon 22 and second balloon 24, the lung tissue may be accessed via lumen 26 of cannula 12 to perform a lung procedure, e.g., a lung biopsy, through lumen 26 of cannula 12 by removing sealant applicator 16 from cannula hub 18 and removing stylet 14 from lumen 26 of cannula 12.

At step S208, after reinstalling sealant applicator 16, for example (if previously removed), additional actuations of first piston 42 and second piston 44 of sealant applicator 16 inflates the pair of balloons 22, 24 with a second, i.e., additional, amount of the two-component sealant that is sufficient to rupture the pair of balloons 22, 24 so as to comingle the first sealant component 35-1 and the second sealant component 35-2 of the two-component sealant to form a sealant gel at the site of the pleural layers 58, 62, so as to adhere the pleural layers 58, 62 together.

Step S208 may be performed, for example, by actuating first piston 42 and second piston 44, separately or simultaneously, to supply the second amount of the first sealant component 35-1 of the two-component sealant to first balloon 22 to rupture first balloon 22, and to supply the second amount of second sealant component 35-2 of the two-component sealant to second balloon 24 to rupture second balloon 24.

At step S210, cannula 12 and the ruptured pair of balloons 22, 24 are withdrawn along access opening 54 to aid in comingling the first sealant component 35-1 and the second sealant component 35-2 of the two-component sealant at the pleural layers 58, 62 and in access opening 54. In one implementation of the method, step S210, i.e., the step of withdrawing, will immediately follow the step S208 that results in the rupture of the pair of balloons 22, 24.

As used herein, the terms "substantially", "generally", "slightly", and other words of degree, are relative modifiers intended to indicate permissible variation from the characteristic so modified. Such terms are not intended to be limited to the absolute value of the characteristic which it modifies, but rather possessing more of the physical or functional characteristic than the opposite.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for use in a lung access procedure to aid in preventing pneumothorax, comprising:
   providing a cannula having a pair of balloons, the pair of balloons including a first balloon longitudinally spaced from a second balloon along the cannula;
   inserting the cannula along an access opening and through pleural layers of a patient, with the first balloon and the second balloon of the pair of balloons respectively positioned on opposite sides of the pleural layers;
   inflating the pair of balloons with a first amount of a two-component sealant to compress the pleural layers together; and
   inflating the pair of balloons with a second amount of the two-component sealant that is sufficient to rupture the pair of balloons so as to comingle a first sealant component and a second sealant component of the two-component sealant at the site of the pleural layers so as to adhere the pleural layers together.

2. The method of claim 1, further comprising withdrawing the cannula and the pair of ruptured balloons along the access opening to aid in comingling the first sealant component and the second sealant component of the two-component sealant at the pleural layers and in the access opening.

3. The method of claim 2, wherein the step of withdrawing follows the step of inflating the pair of balloons with the second amount of the two-component sealant to rupture the pair of balloons.

4. The method of claim 1, wherein the first balloon is inflated with the first sealant component of the two-component sealant at each of the first amount and the second amount, and the second balloon is inflated with the second sealant component of the two-component sealant at each of the first amount and the second amount.

5. The method of claim 1, wherein the first sealant component comingles with the second sealant component to form a sealant gel.

6. The method of claim 1, wherein the first sealant component has at least two N-hydroxysuccinimide (NHS) ester groups and the second sealant component has at least two amine groups.

7. The method of claim 1, wherein the first sealant component is polyethylene glycol (PEG) succinimidyl succinate and the second sealant component is taken from a group consisting of albumin, polyethylenimine (PEI), and a functionalized PEG having at least two amine groups.

8. The method of claim 1, wherein following the compression of the pleural layers together and prior to rupturing the pair of balloons, the method further comprising accessing lung tissue via a lumen of the cannula.

9. The method of claim 1, wherein the steps of inflating are performed by the steps of:
   connecting a sealant applicator to the cannula; and
   actuating an actuator of the sealant applicator to simultaneously supply the first sealant component of the two-component sealant to the first balloon and supply the second sealant component of the two-component sealant to the second balloon.

10. The method of claim 9, wherein the step of actuating the actuator comprises depressing a plunger handle of a syringe-type applicator.

* * * * *